United States Patent [19]

Heusser et al.

[11] 4,381,313
[45] Apr. 26, 1983

[54] PHENYLALKANOIC COMPOUNDS AND THERAPEUTIC USE THEREOF

[75] Inventors: Jean Heusser, Adliswil; Max Glasbrenner, Zurich, both of Switzerland

[73] Assignee: Hommel AG, Adliswil, Switzerland

[21] Appl. No.: 268,221

[22] Filed: May 29, 1981

Related U.S. Application Data

[63] Continuation-in-part of Ser. No. 618,636, Oct. 1, 1975, abandoned.

[30] Foreign Application Priority Data

Oct. 8, 1974 [CH] Switzerland .............. 13516/74
Oct. 8, 1974 [CH] Switzerland .............. 13517/74

[51] Int. Cl.³ .............. C07C 101/00; A61K 31/215
[52] U.S. Cl. ...................... 424/308; 560/105
[58] Field of Search .................. 560/105; 424/308

[56] References Cited

U.S. PATENT DOCUMENTS

| | | | |
|---|---|---|---|
| 3,228,831 | 1/1966 | Nicholson | 560/105 |
| 3,349,114 | 10/1967 | Heusser et al. | 560/105 |
| 3,422,102 | 1/1969 | Morren et al. | 560/105 |
| 3,452,079 | 6/1969 | Shen | 560/105 |
| 3,965,161 | 6/1976 | Kogure | 560/105 |

Primary Examiner—Robert Gerstl
Attorney, Agent, or Firm—Joseph G. Kolodny

[57] ABSTRACT

Novel phenylalkanoic compounds of the formula I

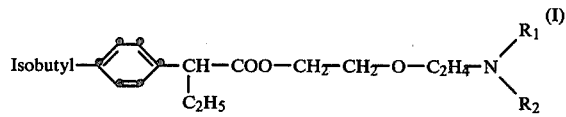

wherein $R_1$ and $R_2$ independently from each other represent hydrogen or alkyl with 1 to 8 carbon atoms, salts of such compounds and salts thereof, therapeutic uses of the phenylalkanoic compounds, or of the pharmacologically safe salts thereof for treating inflammatory diseases, tussive states, pain symptoms and pyretic diseases and pharmaceutical composition containing the phenylalkanoic compounds or the pharmacologically safe salts together with a carrier and an optional adjuvant or additive.

8 Claims, No Drawings

PHENYLALKANOIC COMPOUNDS AND THERAPEUTIC USE THEREOF

This is a continuation-in-part of our copending application Ser. No. 618,636, filed Oct. 1, 1975 now abandoned.

BACKGROUND AND OBJECTS OF THE INVENTION

This invention is directed to novel substituted phenylalkanoic acids and their derivatives, to methods of preparing such acids and derivatives, and to their use in pharmaceutical compositions.

During recent years increasing use has been made of phenylalkanoic acids in human medicine for treating inflammatory and pyretic diseases as well as for relieving pain. While having a satisfactory effectiveness, some of these known compounds exhibit substantial and undesirable side effects.

It is, therefore, a primary object of the invention to provide for phenylalkanoic compounds which have a satisfactory anti-inflammatory, antitussive, analgesic and antipyretic activity while showing substantially no undesirable side effects.

A further object is a pharmaceutical preparation containing the novel phenylalkanoic compounds in a form suitable for therapeutic administration.

Still another object of the invention is a novel method of treating inflammatory diseases, tussive states, pain symptoms and pyretic diseases.

Other objects will become apparent as the specification proceeds.

SUMMARY OF INVENTION

In accordance with the above and further objects it was found that compounds of the formula (I)

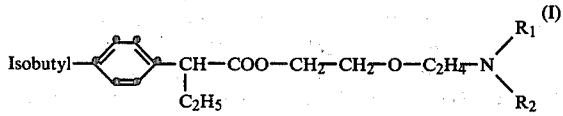

wherein $R_1$ and $R_2$ independently from each other represent hydrogen or alkyl with 1 to 8 carbon atoms and pharmacologically safe salts of such formula (I) compounds provide excellent anti-inflammatory, antitussive, analgesic and antipyretic properties.

It is of notable interest and constitutes a particular advantage of the invention that the formula (I) compounds defined above, if compared to prior art phenylalkanoic acid esters, provide a remarkably improved compatibility, and show substantially no undesirable side effects. Thus, the novel compounds are excellently suited for treatment of inflammatory diseases, cough and pain symptoms and pyretic diseases in human medicine and can be used in combination with pharmaceutical additives or adjuvants for the production of pharmaceutical compositions containing one or more compounds of formula (I).

The following compound is particularly preferred: the diethylaminoethoxyethyl ester of 2-(4-isobutylphenyl)butyric acid and the pharmacologically safe salts of this compound.

Formula (I) compounds are obtained according to an embodiment of the invention by alkylating a compound of formula (II)

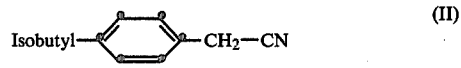

by reaction with a compound yielding the $C_2H_5$-group, the reaction being effected in the presence of a strong base, preferably a highly concentrated solution of sodium hydroxide, and of a catalyst, preferably triethylbenzyl ammonium chloride. The resulting intermediate product of formula (III)

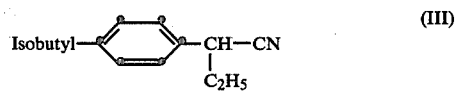

is separated from unreacted starting formula (II) compound by means of using benzaldehyde. Then, the resulting product is hydrolyzed (saponification) under acid conditions, preferably by means of a mixture of acetic acid (e.g. in the form of glacial acetic acid), sulphuric acid, and water.

The 2-(4-isobutylphenyl)-butyric acid obtained, or a functional derivative thereof, is then reacted with a compound of formula (IV)

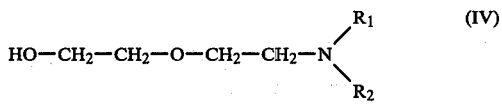

where $R_1$ and $R_2$ are as defined above.

According to a preferred embodiment of the invention, the 2-(4-isobutylphenyl)butyric acid is first transformed into the corresponding acid halide by reaction with a halogenating agent, thionylchloride being a particularly preferred halogenating agent for that purpose. These acid halides are subsequently reacted with a compound of the formula (IV) to give the corresponding compound of formula (I).

The compounds thus obtained may be converted into their pharmacologically safe or acceptable salts by treating a compound of formula (I) with an acid.

DETAILED DESCRIPTION OF THE INVENTION

The pharmacological properties of the compounds according to the invention as well as their toxicity were determined by animal tests and compared with known compounds that have similar effects. The results obtained are reported in the Tables below. The test substance used is designated as "HH 10 120", that is, the diethylaminoethoxyethyl ester of 2-(4-isobutylphenyl)-butyric acid. The prior art substances used for comparison were: Ibuprofen, Butazone (phenylbutazone) and Codein phosphate.

TABLE I

| Substances | Activity sc | Activity p.o. | Hot-Plate-Test sc | Hot-Plate-Test p.o. | Stretch-Spasm-Test sc | Tailburning Test sc | Tailburning Test p.o. | Antipyretic Yeast sc | Antipyretic Yeast p.o. | Antipyretic Witt-Petone p.o. | Macrodex sc | Carragenin p.o. | $DL_{50}$ sc | $DL_{50}$ p.o. | Spasmolysis | Erythema UV-Lamp sc |
|---|---|---|---|---|---|---|---|---|---|---|---|---|---|---|---|---|
| HH 10 120 | 1 | 1 | 6 | 2 | 2 | 2 | 2 | 0.5 | 1–2 | 1.3 | 2 | 0.8 | 1 | 1 | 1 | 1 |
| Ibuprofen | 1 | 1 | 1 | 1 | | 1 | 1 | 1 | | | 1 | | 1 | 1 | | 1 |
| Butazone | | | 2 | | | | | | 1 | 1 | 2 | 1 | | | | 0.9 |
| Codein phosph. | | | 12 | 20 | 4 | 12 | 20 | | | | | | | | | |

HH 10 120 = diethylaminoethoxyethyl ester of 2-(4-isobutylphenyl)butyric acid
Ibuprofen = 2-(p-isobutylphenyl)propionic acid
Butazone = 4-butyl-1,2-diphenylpyrazolidine-3,5-dione
sc = subcutaneous administration
p.o. = per os, oral administration
$DL_{50}$ = toxicity (average)

TABLE II

| Substances | Antitussive Effect po | Antitussive Effect iv |
|---|---|---|
| HH 10 120 | 1 | 1 |
| Butamirate citrate | 1 | 8 |
| Codein phosphate | 1 | |

The numbers which are set forth in Tables I and II are relative values showing the effectiveness of the particular compounds being compared. The number six, when compared to the number one clearly means that one compound may be six times more effective than another compound when tested under the same conditions.

The test procedures employed by applicants when comparing the compounds of the present invention against prior art compounds are conventional. Further information can be found in the following literature references:

(1) Acute Toxicity
  J. T. Lichtfield and F. Wilcoxon J. Pharmacol. Exptl. Therap. 96, 99–113 (1949)
(2) Hotplate-Test
  Paul A. J. Janssen and Anton H. Jagenau J. Pharm. Pharmacol. 9, 381–400 (1957)
(3) Stretch-Spasm-Test
  L. B. Witkin et al J. Pharmacol. Exptl. Therap. 133, 400–408 (1961)
(4) Tailburning-Test
  L. Ther et al. Deutsche Apoth. 2tg. 103, 514–520 (1963)
(5) Yeast-Test
  U. M. Teotino et al J. Med Chem. 6, 248–250 (1963)
(6) Carrageenin-Test
  Charles A. Winter et al Proc. Soc. exp. Biol. 111, 544–547 (1962)
(7) Antitussive-Test
  R. Domenjoz Arch. Exptl. Path. Pharmakol. 215, 19–24 (1952).

The compounds of formula (I) as well as their pharmacologically safe salts may be manufactured in a manner known per se to produce pharmaceutical compositions using pharmaceutically acceptable carriers and adjuvants. The novel compounds are suitable both for oral as well as rectal and parenteral administration and for topical application.

Tablets, film tablets, dragees, coated pills, capsules, syrups, liquid preparations for dropwise dispensation and elixirs are particularly suited for oral administration. The conventional substances for preparation of pharmaceutical compositions, such as magnesium carbonate or magnesium stearate, calcium carbonate, sugar, lactose, pectin, dextrin, starch, gelatin, gum tragacanth, methyl cellulose or sodium carboxymethyl cellulose, may be used as carriers. In addition, diluents, flavoring additives, solvatizing agents, lubricants, suspending agents, binders or other conventional adjuvants for tablets may be added. Compositions in solid form suitable for oral administration preferably include from about 5 or 10 up to 99% of the active compound or mixture of compounds. Solutions, suspensions or emulsions are suitable forms of liquid compositions. Aqueous suspensions suitable for oral administration may be prepared by using natural or synthetic gums ("caoutchouc"), ethyl cellulose or other known suspending agents. Preferably, such preparations also include a flavoring agent.

For oral administration the daily dose for a human adult of average weight preferably is from 100 to 600 mg and is administered in three portions of from 100 to 200 mg each.

Suppositories prepared with conventional carriers and lubricants are particularly suited for rectal administration. The dose for the human adult of average weight generally is between 100 and 300 mg per suppository.

Liquid preparations, such as solutions, suspensions or emulsions, are suitable for parenteral administration. Such compositions include dispersions in a non-toxic carrier, for example, peanut oil or sterile water, preferably in combination with a non-ionic surfactant, such as a fatty acid ester of a polyhydroxy compound. Ampuls, phials or infusion solutions are suitable for parenteral administration. If required, such compositions may be made isotonic by addition of suitable conventional agents. For parenteral administration a dose of from 10 to 50 mg per ampul is preferred.

The compounds of formulae (I) and (II) may also be used for preparing compositions suitable for topical application. Salves, linaments and lotions prepared with the conventional carriers and adjuvants are particularly suitable for such topical application.

The following examples are illustrative but not limitative of the invention. Percentages are by weight. Where the term "ether" is used without other indication this is intended to refer to diethyl ether. The symbols "g", "mg" and "ml" stand for grams, milligrams and milliliters, respectively. Temperatures are in degree Centigrade (°C.).

EXAMPLE 800 mg of isobutyl benzene, 197 g of paraformaldehyde, 150 g of zinc chloride and 906 g of glacial acetic acid are heated on a water bath at 80° C. while dry gaseous hydrogen chloride is introduced during 7 hours. Then, the mixture is cooled, diluted with water, and the oil that separates is extracted with ether. The ether layer is washed with sodium carbonate solution. After separating of the aqueous layer, the ether is removed from the organic phase by evaporation. This yields 527 g of crude 4-isobutylbenzyl chloride.

527 g of 4-isobutylbenzyl chloride, 153 g of sodium cyanide and 720 ml of dimethylsulfoxide are agitated for 6 hours at 40° C. The mixture is cooled and then diluted with water. An oily layer separates and is extracted with ether. The ether solution is subjected to fractionation and yields 367 g of 4-isobutylphenyl acetonitrile.

550 g of ethyl bromide are added drop-wise to 470 g of 4-isobutylphenyl acetonitrile, 1550 g of a 50% solution of sodium hydroxide and 11.4 g of triethylbenzyl ammonium chloride. The addition is complete within 2 hours. During this addition, the temperature must be controlled such that it does not exceed 40° C. The mixture is agitated for 10 hours at 40° C. After cooling of the mixture, the alkaline phase is discarded and the organic layer is washed with water until neutral. Fractionation yields 536 g of crude 2-(4-isobutylphenyl)-butyronitrile.

143 g of crude 2-(4-isobutylphenyl)butyronitrile, 50 g of benzaldehyde, 10.7 g of sodium and 358 ml of methanol are left to stand for 2 days and are then diluted with water and extracted with ether. The ether layer is extracted with a saturated solution of sodium hydrogen sulfite until no benzaldehyde can be detected anymore. The ether solution is subjected to fractionation and yields 133 g of pure 2-(4-isobutylphenyl)butyronitrile.

337 g of 2-(4-isobutylphenyl)butyronitrile, 337 ml of concentrated sulphuric acid, 337 ml of glacial acetic acid and 337 ml of water are hydrolyzed under reflux for 8 hours. Then, the mixture is cooled, diluted with water, and the oil that separates is extracted with ether. The ether layer is washed with water until neutral and then subjected to fractionation.

The yield is 433 g of 2-(4-isobutylphenyl)butyric acid. Boiling point: 134°-138° C./0.15 mm Hg. Refractive index $n_D^{20} = 1.5060$.

Elementary analysis: Calculated for $C_{14}H_{20}O_2$: C=76.3%, H=9.2%; Found: C=77.3%, H=9.8%.

110 g of 2-(4-isobutylphenyl)butyric acid and 89 g of thionyl chloride are heated on a water bath until the gas evolution ceases. An excess of thionyl chloride is removed by distillation, A residue of 117 g of 2-(4-isobutylphenyl)butyric chloride is obtained.

117 g of 2-(4-isobutylphenyl)butyric chloride are dissolved in 40 ml of toluene. A solution of 78 g of diethylamino-ethoxyethanol in 40 ml of toluene is added slowly to this solution while an exothermic reaction is observed which leads to an increase of the temperature of the solution.

The mixture is then refluxed for 7 hours. After cooling of the mixture, 400 ml of water are added and the pH is adjusted to 9 with concentrated ammonia solution. After thoroughly mixing the solution, the toluene layer is separated and washed with water until neutral. The toluene layer is treated with activated charcoal and the toluene is removed from the filtered solution by distillation.

165 g of the diethylaminoethoxyethyl ester of 2-(4-isobutylphenyl)butyric acid are obtained ($n_D^{20} = 1.4876$).

142 g of that basic ester are dissolved in 375 ml of acetone and added to a solution of 75 g of citric acid in 375 ml of acetone. After a period of time, the citrate of the ester starts to crystallize. The product is filtered and washed with isopropyl ether. The citrate of the ester is recrystallized from acetone. The melting point of the citrate is 83°-84° C. (corrected).

Elementary analysis: Calculated for $C_{28}H_{45}NO_{10}$: C=60.5%, H=8.2%, N=2.5%; Found: C=60.4%, H=8.3%, N=2.6%.

What is claimed is:

1. A compound of the formula (I)

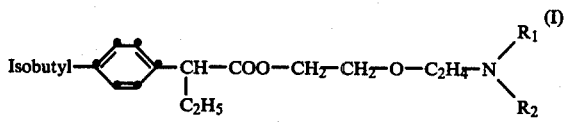

wherein $R_1$ and $R_2$ independently from each other represent hydrogen or alkyl with 1 to 8 carbon atoms and pharmacologically safe salts of such compound.

2. A compound according to claim 1, which is the diethylaminoethoxyethyl ester of 2-(4-isobutylphenyl)-butyric acid and pharmacologically safe acid addition salts thereof.

3. A pharmaceutical composition comprising at least one compound of the formula (I)

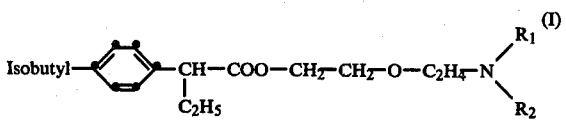

wherein $R_1$ and $R_2$ independently from each other represent hydrogen or alkyl with 1 to 8 carbon atoms or a pharmacologically safe salt of formula (I) compound; said composition further comprising an anti-inflammatorically, antitussively, analgesically and antipyretically effective amount of the active ingredient together with substances selected from the group consisting of pharmaceutical carriers suitable for oral, for parenteral or for topical administration.

4. A pharmaceutical composition according to claim 3 which contains diethylaminoethoxyethyl ester of 2-(4-isobutylphenyl)butyric acid or a pharmacologically safe salt thereof.

5. A method of treating inflammatory diseases, pain symptoms, tussive states and pyretic diseases of a human patient, said method comprising administering an amount effective for curing or alleviating said diseases, to said patient an effective amount of a pharmaceutical composition comprising at least one compound of formula (I)

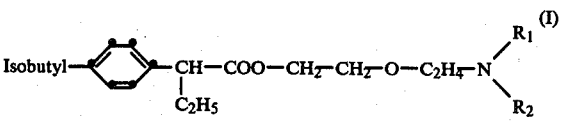

wherein $R_1$ and $R_2$ independently from each other represent hydrogen or alkyl with 1 to 8 carbon atoms, or a pharmacologically safe salt thereof, said composition further comprising a substance selected from the group consisting of pharmaceutical carriers suitable for oral, for parenteral or for topical administration.

6. A method according to claim 5, for treating tussuve states of a human patient, which comprises administering to said patient an antitussively effective amount of a pharmaceutical composition comprising at least one compound of formula (I) defined in claim 5 or a pharmacologically safe salt thereof.

7. A method according to claim 5, which comprises administering a pharmaceutical composition comprising the diethylaminoethoxyethyl ester of 2-(4-isobutylphenyl)butyric acid or a pharmacologically safe salt thereof.

8. A method according to claim 6, which comprises administering a pharmaceutical composition comprising the diethylaminoethoxyethyl ester of 2-(4-isobutylphenyl)butyric acid or a pharmacologically safe salt thereof.

* * * * *